(12) United States Patent
Garrigues

(10) Patent No.: US 11,850,144 B1
(45) Date of Patent: Dec. 26, 2023

(54) LIGAMENT DOCKING IMPLANTS AND PROCESSES FOR MAKING AND USING SAME

(71) Applicant: restor3d, Inc., Durham, NC (US)

(72) Inventor: Grant Edward Garrigues, Hinsdale, IL (US)

(73) Assignee: RESTOR3D, INC., Durham, NC (US)

( * ) Notice: Subject to any disclaimer, the term of this patent is extended or adjusted under 35 U.S.C. 154(b) by 0 days.

(21) Appl. No.: 17/936,283

(22) Filed: Sep. 28, 2022

(51) Int. Cl.
*A61F 2/08* (2006.01)
*A61F 2/30* (2006.01)

(52) U.S. Cl.
CPC ........ *A61F 2/0811* (2013.01); *A61F 2/30749* (2013.01); *A61F 2002/0852* (2013.01); *A61F 2002/30784* (2013.01)

(58) Field of Classification Search
CPC ............... A61F 2/0811; A61F 2/30749; A61F 2002/0852; A61F 2002/30784; A61F 2/42; A61F 2002/3093; A61B 17/06; A61B 17/80; A61B 17/061
See application file for complete search history.

(56) References Cited

U.S. PATENT DOCUMENTS

| | | | |
|---|---|---|---|
| 4,440,835 A | 4/1984 | Vignaud | |
| 4,588,574 A | 5/1986 | Felder et al. | |
| 4,829,152 A | 5/1989 | Rostoker | |
| 5,248,456 A | 9/1993 | Evans, Jr. et al. | |
| 6,419,491 B1 | 7/2002 | Ricci | |
| 7,001,672 B2 | 2/2006 | Justin et al. | |
| D595,853 S | 7/2009 | Hanson | |
| 7,632,575 B2 | 12/2009 | Justin et al. | |
| 7,666,522 B2 | 2/2010 | Justin et al. | |
| D623,749 S | 9/2010 | Horton | |
| D653,756 S | 2/2012 | Courtney et al. | |
| 8,142,886 B2 | 3/2012 | Noble et al. | |
| D675,320 S | 1/2013 | Oi | |
| 8,430,930 B2 | 4/2013 | Hunt | |
| 8,457,930 B2 | 6/2013 | Schroeder | |

(Continued)

FOREIGN PATENT DOCUMENTS

KR 301007894 5/2019

OTHER PUBLICATIONS

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).

(Continued)

*Primary Examiner* — Yashita Sharma
(74) *Attorney, Agent, or Firm* — Husch Blackwell LLP; Bryan D. Stewart; Andrew C. Landsman

(57) ABSTRACT

Provided herein are ligament docking implants and methods for making and using the same. In at least one embodiment, the implants include at least one docking recess configured to receive a tissue structure such as a ligament and connect said tissue to the implant via suitable surgical techniques. In at least one embodiment, the docking recesses of the implant include a gyroid architecture that provides for improved mechanical performance and tissue integration. In various embodiments, the present methods of using the ligament docking implants include the use of sutures to connect tissue to the implant via the docking recess.

22 Claims, 14 Drawing Sheets

(56) References Cited

U.S. PATENT DOCUMENTS

| | | |
|---|---|---|
| 8,485,820 B1 | 7/2013 | Ali |
| D692,136 S | 10/2013 | Tyber |
| 8,551,173 B2 | 10/2013 | Lechmann et al. |
| D708,747 S | 7/2014 | Curran et al. |
| 8,775,133 B2 | 7/2014 | Schroeder |
| 8,828,311 B2 | 9/2014 | Medina et al. |
| 8,843,229 B2 | 9/2014 | Vanasse et al. |
| 8,888,485 B2 | 11/2014 | Ali |
| D722,693 S | 2/2015 | Kaufmann et al. |
| 9,034,237 B2 | 5/2015 | Sperry et al. |
| D735,860 S | 8/2015 | Palinchik |
| D736,384 S | 8/2015 | Palinchik |
| 9,180,029 B2 | 11/2015 | Hollister et al. |
| 9,186,257 B2 | 11/2015 | Geisler et al. |
| D745,159 S | 12/2015 | Lin |
| D747,485 S | 1/2016 | Oi |
| 9,271,845 B2 | 3/2016 | Hunt et al. |
| 9,295,562 B2 | 3/2016 | Lechmann et al. |
| 9,308,060 B2 | 4/2016 | Ali |
| 9,339,279 B2 | 5/2016 | Dubois et al. |
| 9,364,896 B2 | 6/2016 | Christensen et al. |
| 9,370,426 B2 | 6/2016 | Gabbrielli et al. |
| 9,415,137 B2 | 8/2016 | Meridew |
| 9,421,108 B2 | 8/2016 | Hunt |
| D767,137 S | 9/2016 | Lin |
| 9,433,510 B2 | 9/2016 | Lechmann et al. |
| 9,433,707 B2 | 9/2016 | Swords et al. |
| 9,545,317 B2 | 1/2017 | Hunt |
| 9,549,823 B2 | 1/2017 | Hunt et al. |
| 9,561,115 B2 | 2/2017 | Elahinia et al. |
| 9,572,669 B2 | 2/2017 | Hunt et al. |
| 9,597,197 B2 | 3/2017 | Lechmann et al. |
| 9,636,226 B2 | 5/2017 | Hunt |
| 9,649,178 B2 | 5/2017 | Ali |
| 9,662,157 B2 | 5/2017 | Schneider et al. |
| 9,662,226 B2 | 5/2017 | Wickham |
| 9,668,863 B2 | 6/2017 | Sharp et al. |
| 9,675,465 B2 | 6/2017 | Padovani et al. |
| 9,688,026 B2 | 6/2017 | Ho et al. |
| 9,694,541 B2 | 7/2017 | Pruett et al. |
| 9,715,563 B1 | 7/2017 | Schroeder |
| 9,757,235 B2 | 9/2017 | Hunt et al. |
| 9,757,245 B2 | 9/2017 | O'Neil et al. |
| 9,782,270 B2 | 10/2017 | Wickham |
| 9,788,972 B2 | 10/2017 | Flickinger et al. |
| D809,661 S | 2/2018 | Mueller et al. |
| 9,907,670 B2 | 3/2018 | Deridder et al. |
| 9,910,935 B2 | 3/2018 | Golway et al. |
| 9,918,849 B2 | 3/2018 | Morris et al. |
| 9,943,627 B2 | 4/2018 | Zhou et al. |
| D829,909 S | 10/2018 | Horton |
| D835,278 S | 12/2018 | Gottlieb |
| 10,183,442 B1 | 1/2019 | Miller |
| 10,245,152 B2 | 4/2019 | Kloss |
| D849,944 S | 5/2019 | Dacosta |
| 10,278,823 B1 | 5/2019 | Xue |
| D850,620 S | 6/2019 | Tyber |
| D855,184 S | 7/2019 | Predick |
| 10,357,377 B2 | 7/2019 | Nyahay |
| D858,769 S | 9/2019 | Barela et al. |
| 10,449,051 B2 | 10/2019 | Hamzey |
| 10,492,686 B2 | 12/2019 | Hunter |
| D877,907 S | 3/2020 | Linder et al. |
| D878,589 S | 3/2020 | Linder et al. |
| D878,590 S | 3/2020 | Linder et al. |
| D879,295 S | 3/2020 | Abbasi |
| D879,961 S | 3/2020 | Linder et al. |
| D881,665 S | 4/2020 | Zemel et al. |
| 10,624,746 B2 | 4/2020 | Jones et al. |
| 10,667,924 B2 | 6/2020 | Nyahay |
| 10,744,001 B2 | 8/2020 | Sack |
| 10,772,732 B1 | 9/2020 | Miller et al. |
| D899,900 S | 10/2020 | Blanco |
| 10,940,015 B2 | 3/2021 | Sack |
| D920,515 S | 5/2021 | Miller |
| D920,516 S | 5/2021 | Miller |
| D920,517 S | 5/2021 | Miller |
| 11,026,798 B1 | 6/2021 | Miller |
| 11,033,394 B2 | 6/2021 | Hamzey |
| 11,135,771 B1 | 10/2021 | Reith |
| D938,033 S | 12/2021 | Dang |
| 11,353,277 B2 | 6/2022 | Muceus |
| 11,439,726 B2 | 9/2022 | Spence |
| 11,471,203 B2 | 10/2022 | Sutika |
| 2004/0064192 A1* | 4/2004 | Bubb .................. A61M 1/77 623/23.5 |
| 2004/0148032 A1 | 7/2004 | Rutter et al. |
| 2006/0249875 A1 | 11/2006 | Robb et al. |
| 2007/0118243 A1 | 5/2007 | Schroeder et al. |
| 2007/0123988 A1* | 5/2007 | Coughlin .............. A61F 2/0811 623/17.14 |
| 2008/0206297 A1 | 8/2008 | Roeder et al. |
| 2009/0093668 A1 | 4/2009 | Marten et al. |
| 2009/0182430 A1 | 7/2009 | Tyber et al. |
| 2010/0137990 A1 | 6/2010 | Apatsidis et al. |
| 2010/0168798 A1 | 7/2010 | Clineff et al. |
| 2010/0286791 A1 | 11/2010 | Goldsmith |
| 2011/0144752 A1 | 6/2011 | Defelice et al. |
| 2011/0190898 A1 | 8/2011 | Lenz |
| 2011/0224796 A1 | 9/2011 | Weiland et al. |
| 2011/0230974 A1 | 9/2011 | Musani |
| 2012/0064288 A1 | 3/2012 | Nakano et al. |
| 2012/0215310 A1 | 8/2012 | Sharp et al. |
| 2013/0068968 A1 | 3/2013 | Daniel |
| 2013/0123935 A1 | 5/2013 | Hunt et al. |
| 2013/0158651 A1 | 6/2013 | Hollister et al. |
| 2013/0197657 A1 | 8/2013 | Anca et al. |
| 2013/0218282 A1 | 8/2013 | Hunt |
| 2013/0274890 A1 | 10/2013 | Mckay |
| 2014/0107785 A1 | 4/2014 | Geisler et al. |
| 2014/0107786 A1 | 4/2014 | Geisler et al. |
| 2014/0236299 A1 | 8/2014 | Roeder et al. |
| 2014/0277443 A1 | 9/2014 | Fleury et al. |
| 2014/0277452 A1 | 9/2014 | Skaer |
| 2014/0288650 A1 | 9/2014 | Hunt |
| 2014/0336680 A1 | 11/2014 | Medina et al. |
| 2014/0371863 A1 | 12/2014 | Vanasse et al. |
| 2015/0105858 A1 | 4/2015 | Papay et al. |
| 2015/0282945 A1 | 10/2015 | Hunt |
| 2015/0282946 A1 | 10/2015 | Hunt |
| 2015/0320461 A1 | 11/2015 | Ehmke |
| 2015/0335434 A1 | 11/2015 | Patterson et al. |
| 2015/0343709 A1 | 12/2015 | Gerstle et al. |
| 2015/0351915 A1 | 12/2015 | Defelice et al. |
| 2016/0008139 A1 | 1/2016 | Siegler |
| 2016/0051371 A1 | 2/2016 | Defelice et al. |
| 2016/0089138 A1 | 3/2016 | Early et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213485 A1 | 7/2016 | Schaufler et al. |
| 2016/0213486 A1 | 7/2016 | Nunley et al. |
| 2016/0213487 A1 | 7/2016 | Wilson et al. |
| 2016/0213488 A1 | 7/2016 | Moore et al. |
| 2016/0220288 A1 | 8/2016 | Dubois et al. |
| 2016/0256279 A1 | 9/2016 | Sanders et al. |
| 2016/0256610 A1 | 9/2016 | Zhou et al. |
| 2016/0270931 A1 | 9/2016 | Trieu |
| 2016/0287388 A1 | 10/2016 | Hunt et al. |
| 2016/0303793 A1 | 10/2016 | Ermoshkin et al. |
| 2016/0333152 A1 | 11/2016 | Cook et al. |
| 2016/0374829 A1 | 12/2016 | Vogt et al. |
| 2017/0014169 A1 | 1/2017 | Dean et al. |
| 2017/0020685 A1 | 1/2017 | Geisler et al. |
| 2017/0036403 A1 | 2/2017 | Ruff et al. |
| 2017/0042697 A1 | 2/2017 | Mcshane, III et al. |
| 2017/0056178 A1 | 3/2017 | Sharp et al. |
| 2017/0056179 A1 | 3/2017 | Lorio |
| 2017/0066873 A1 | 3/2017 | Gardet |
| 2017/0105844 A1 | 4/2017 | Kuyler et al. |
| 2017/0156880 A1 | 6/2017 | Halverson et al. |
| 2017/0165085 A1 | 6/2017 | Lechmann et al. |
| 2017/0165790 A1 | 6/2017 | Mccarthy et al. |
| 2017/0172758 A1 | 6/2017 | Field et al. |

(56) References Cited

U.S. PATENT DOCUMENTS

| | | |
|---|---|---|
| 2017/0182222 A1 | 6/2017 | Paddock et al. |
| 2017/0209274 A1 | 7/2017 | Beerens et al. |
| 2017/0216035 A1 | 8/2017 | Hunt |
| 2017/0216036 A1 | 8/2017 | Cordaro |
| 2017/0239054 A1 | 8/2017 | Engstrand et al. |
| 2017/0239064 A1 | 8/2017 | Cordaro |
| 2017/0245998 A1 | 8/2017 | Padovani et al. |
| 2017/0252165 A1 | 9/2017 | Sharp et al. |
| 2017/0258606 A1 | 9/2017 | Afzal |
| 2017/0282455 A1 | 10/2017 | Defelice et al. |
| 2017/0296244 A1 | 10/2017 | Schneider et al. |
| 2017/0319344 A1 | 11/2017 | Hunt |
| 2017/0323037 A1 | 11/2017 | Schroeder |
| 2017/0333205 A1 | 11/2017 | Joly et al. |
| 2017/0354510 A1 | 12/2017 | O'Neil et al. |
| 2017/0354513 A1 | 12/2017 | Maglaras et al. |
| 2017/0355815 A1 | 12/2017 | Becker et al. |
| 2017/0360488 A1 | 12/2017 | Kowalczyk et al. |
| 2017/0360563 A1 | 12/2017 | Hunt et al. |
| 2017/0360578 A1 | 12/2017 | Shin et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0008419 A1 | 1/2018 | Tyber et al. |
| 2018/0022017 A1 | 1/2018 | Fukumoto et al. |
| 2018/0064540 A1 | 3/2018 | Hunt |
| 2018/0085230 A1 | 3/2018 | Hunt |
| 2018/0104063 A1 | 4/2018 | Asaad |
| 2018/0110593 A1 | 4/2018 | Khalil |
| 2018/0110626 A1 | 4/2018 | Mcshane, III et al. |
| 2018/0110627 A1 | 4/2018 | Sack |
| 2018/0117219 A1 | 5/2018 | Yang et al. |
| 2018/0147319 A1 | 5/2018 | Colucci-Mizenko et al. |
| 2018/0280140 A1 | 10/2018 | Jones |
| 2018/0289515 A1 | 10/2018 | Nemes et al. |
| 2019/0167433 A1 | 6/2019 | Allen |
| 2019/0262101 A1 | 8/2019 | Shanjani et al. |
| 2019/0343652 A1 | 11/2019 | Petersheim et al. |
| 2020/0000595 A1 | 1/2020 | Jones |
| 2020/0030102 A1 | 1/2020 | Mullens et al. |
| 2020/0046512 A1 | 2/2020 | Newman et al. |
| 2020/0085452 A1 | 3/2020 | Siegler |
| 2020/0085585 A1 | 3/2020 | Siegler |
| 2020/0155321 A1 | 5/2020 | Dikovsky |
| 2020/0171752 A1 | 6/2020 | Rogren |
| 2020/0171753 A1 | 6/2020 | Satko |
| 2021/0216683 A1 | 7/2021 | Rai |
| 2021/0298908 A1 | 9/2021 | Holmes |
| 2021/0340334 A1 | 11/2021 | Portela |
| 2022/0023048 A1 | 1/2022 | Nolens |
| 2022/0087670 A1 | 3/2022 | Selmoune |
| 2022/0134639 A1 | 5/2022 | Allen |
| 2022/0142783 A1 | 5/2022 | Ahmadi |
| 2022/0168109 A1 | 6/2022 | Giordano |
| 2022/0296386 A1 | 9/2022 | Fang |

OTHER PUBLICATIONS

Rozema et al., The effects of different steam-sterilization programs on material properties of poly(I-lactide), Journal of Applied Biomaterials, vol. 2, 23-28 (1991) (Year: 1991).

Alt, Sami. "Design for Sterilization Part 1: Steam Sterillization." Material, Material Technology Blog, Jun. 3, 2016, www.material-technology.com/single-post/2016/05/24/Design-for-Sterilization-part-1-Steam-Sterillization.

Ducheyne, Paul. "Comprehensive Biomaterials." Comprehensive Biomaterials, vol. 1, Elsevier, 2011, pp. 135-135.

Anat Ratnovsky et al., Mechanical Properties of Different Airway Stents, Med. Eng'g. Physics, Mar. 2011, at 408., http://www.medengphys.com/article/S1350-4533(15)00042-9/fulltext.

Andrew T. Miller et al., Fatigue of Injection Molded and 30 Printed Polycarbonate Urethane in Solution, 108 Polymer 121 (2017).

Andrew T. Miller et al., Deformation and Fatigue of Tough 30 Printed Elastomer Scaffolds Processed by Fused 3 Deposition Modeling and Continuous Liquid Interface Production, 75 J. Mechanical Behavior Biomedical Materials 1 (2017).

Ortho Spine News, "SeaSpine Announces 25,000th NanoMetalene Implantation", first available Dec. 18, 2019. (https://orthospinenews.com/2019/12/18/seaspine-announces-25000th-nanometalene-implantation/) (Year: 2019).

Restor3d, "Products", first available Sep. 28, 2020. (https://web.archive.org/web/20200928123335/https:/restor3d.com/products) (Year: 2020).

Ortho Spine News, "Nvision Biomedical Technologies: First FDA Clearance for Osteotomy Wedge System", first available Oct. 28, 2020. (https://orthospinenews.com/2020/10/28/nvision-biomedical-technologies-first-fda-clearance-for-osteotomy-wedge-system-made-of-peek-optima-ha-enhanced/) (Year: 2020).

Sina, "Application logic of triple periodic minimum surface", first available Oct. 24, 2020. (https://k.sina.com.cn/article_2422410454_90630cd6001 00tlbm.html?from=science) (Year: 2020).

3D Adept Media, "Johnson & Johnson Medical", first available Sep. 17, 2018. (https://3dadept.com/johnson-johnson-medical-has-acquired-3d-printed-spmplants-special ist-emerging-implant-technologies/) (Year: 2018).

Additive Orthopaedics, "Additive Orthopaedics 3d Printed Cotton Bone Segment", first available Sep. 19, 2020. (https://web.archive.org/web/20200919145251/https:/www.additiveorthopaedics.com/our-products/cotton/) (Year: 2020).

Indiamart, "Anterior Cervical Fusion Cage for Spine Surgery", first accessed Dec. 9, 2020. (https://www.indiamart.com/proddetail/ anterior-cervical-fusion-cage-12402896897 .html) (Year: 2020).

Instagram, "restor3d", first available Jul. 21, 2020. (https://www.instagram.com/p/CC6dztOAKcM/?utm_source=ig_web_link) (Year: 2020).

* cited by examiner

LIGAMENT DOCKING IMPLANTS AND PROCESSES FOR MAKING AND USING SAME

BACKGROUND

Joint replacement surgery, such as arthroplasty and arthrodesis procedures, amongst other types of procedures, involves replacement of a degraded or diseased or otherwise nonfunctioning existing joint section in a patient with an artificial joint implant that includes some or all parts of a particular joint and/or surrounding sections of bones. Such procedures may restore functionality to the joint, relieve pain, fuse essential tissues to the replacement joint, and/or promote ossification. It is preferable for the prosthesis choice to be nontoxic yet resistant, compatible, and durable. These procedures are particularly difficult due to challenges with reattaching essential tissues (such as ligaments and tendons). For example, implants used in the exemplary procedures mentioned above my encompass bone where tissue may have previously (or would ideally) attach.

As a result, there is a long-felt, but unsolved need for improved medical devices for joint replacement surgeries and methods of producing and installing the same.

BRIEF SUMMARY OF THE DISCLOSURE

Briefly described, aspects of the present disclosure generally relate to implants configured for improved tissue (e.g., ligament) attachment, ligament in-growth, and processes for making and using the same.

The present disclosure relates to a method for securing tissue to an implant and comprising, according to a first aspect, (i) preparing a target site of a subject; (ii) inserting an implant into the target site, the implant comprising (a) a docking recess configured to receive one or more tissue structures and defining at least one opening extending from the docking recess through an outer surface of the implant, wherein the at least one opening is configured to receive a suture; and (b) the outer surface comprising a porous osteointegration region and at least one smooth region, the at least one smooth region comprising a lower coefficient of friction than the porous osteointegration region; (iii) stitching the suture to the one or more tissue structures; and (iv) securing the one or more tissue structures to the implant by (a) threading the suture through the implant via the at least one opening; (b) inserting the one or more tissue structures into the docking recess; and (c) securing the suture over the at least one smooth region.

According to a second aspect, the method of the first aspect or any other aspect, wherein the one or more tissue structures comprise a ligament of the subject.

According to a third aspect, the method of the second aspect or any other aspect, wherein the one or more tissue structures comprise a portion of bone attached to the ligament of the subject.

According to a fourth aspect, the method of the third aspect or any other aspect, wherein the implant comprises a transition area between the outer surface and the docking recess.

According to a fifth aspect, the method of the fourth aspect or any other aspect, wherein the transition area comprises a perimeter defining a depression or fossa.

According to a sixth aspect, the method of the fourth aspect or any other aspect, wherein the docking recess comprises a back surface opposite the transition area.

According to a seventh aspect, the method of the sixth aspect or any other aspect, wherein the back surface defines the at least one opening.

According to an eighth aspect, the method of the seventh aspect or any other aspect, wherein the docking recess comprises a depth between the transition area to the back surface.

According to a ninth aspect, the method of the eighth aspect or any other aspect, wherein the depth is 2 millimeters to 30 millimeters.

According to a tenth aspect, the method of the eighth aspect or any other aspect, wherein the docking recess comprises one or more side surfaces between the transition area and the back surface.

According to an eleventh aspect, the method of the tenth aspect or any other aspect, wherein at least one of the back surface and the one or more side surfaces comprise a porous structure.

According to a twelfth aspect, the method of the eleventh or any other aspect, wherein the porous structure comprises a textured structure.

The present disclosure also relates to an implant that, in some embodiments, advantageously promote ligament in-growth, such as, for example, an elbow implant by including a ligament docking feature. According to a thirteenth aspect, the present disclosure relates to a surgical implant comprising (i) an outer surface comprising a porous osteointegration region and at least one smooth region comprising a lower coefficient of friction than the porous osteointegration region; (ii) a transition area between the outer surface and a docking recess; (iii) a docking recess configured to receive one or more tissue structures and comprising a back surface opposite the transition area and at least one opening defined by the back surface and extending from the back surface through the outer surface and configured to receive a suture stitched to the one or more tissue structures.

According to a fourteenth aspect, the surgical implant of the thirteenth aspect or any other aspect, wherein the transition area comprises a perimeter defining a depression or fossa.

According to a fifteenth aspect, the surgical implant of the fourteenth aspect or any other aspect, wherein the docking recess comprises a depth between the transition area to the back surface.

According to a sixteenth aspect, the surgical implant of the fifteenth aspect or any other aspect, wherein the depth is between 2 millimeters and 30 millimeters.

According to a seventeenth aspect, the surgical implant of the sixteenth aspect or any other aspect, wherein the docking recess comprises one or more side surfaces between the transition area and the back surface.

According to an eighteenth aspect, the surgical implant of the seventeenth aspect or any other aspect, wherein at least one of the back surface and one or more side surfaces comprise a porous structure.

According to a nineteenth aspect, the surgical implant of the eighteenth aspect or any other aspect, wherein the porous structure comprises a textured structure.

According to a twentieth aspect, the surgical implant of the nineteenth aspect or any other aspect, wherein the porous osteointegration region and the porous structure comprise an integrally formed, 3D-printed gyroid structure.

According to a twenty-first aspect, the surgical implant of the twentieth aspect or any other aspect, wherein the surgical implant is designed for use in a patient's elbow.

According to a twenty-second aspect, the surgical implant of the twentieth aspect or any other aspect, wherein the surgical implant is designed for use in a patient's ankle.

According to a twenty-third aspect, the surgical implant of the twentieth aspect or any other aspect, wherein the surgical implant is designed for use in a patient's shoulder.

According to a twenty-fourth aspect, the surgical implant of the twentieth aspect or any other aspect, wherein the surgical implant is designed for use in a patient's hip.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

DETAILED DESCRIPTION

Figure 1:
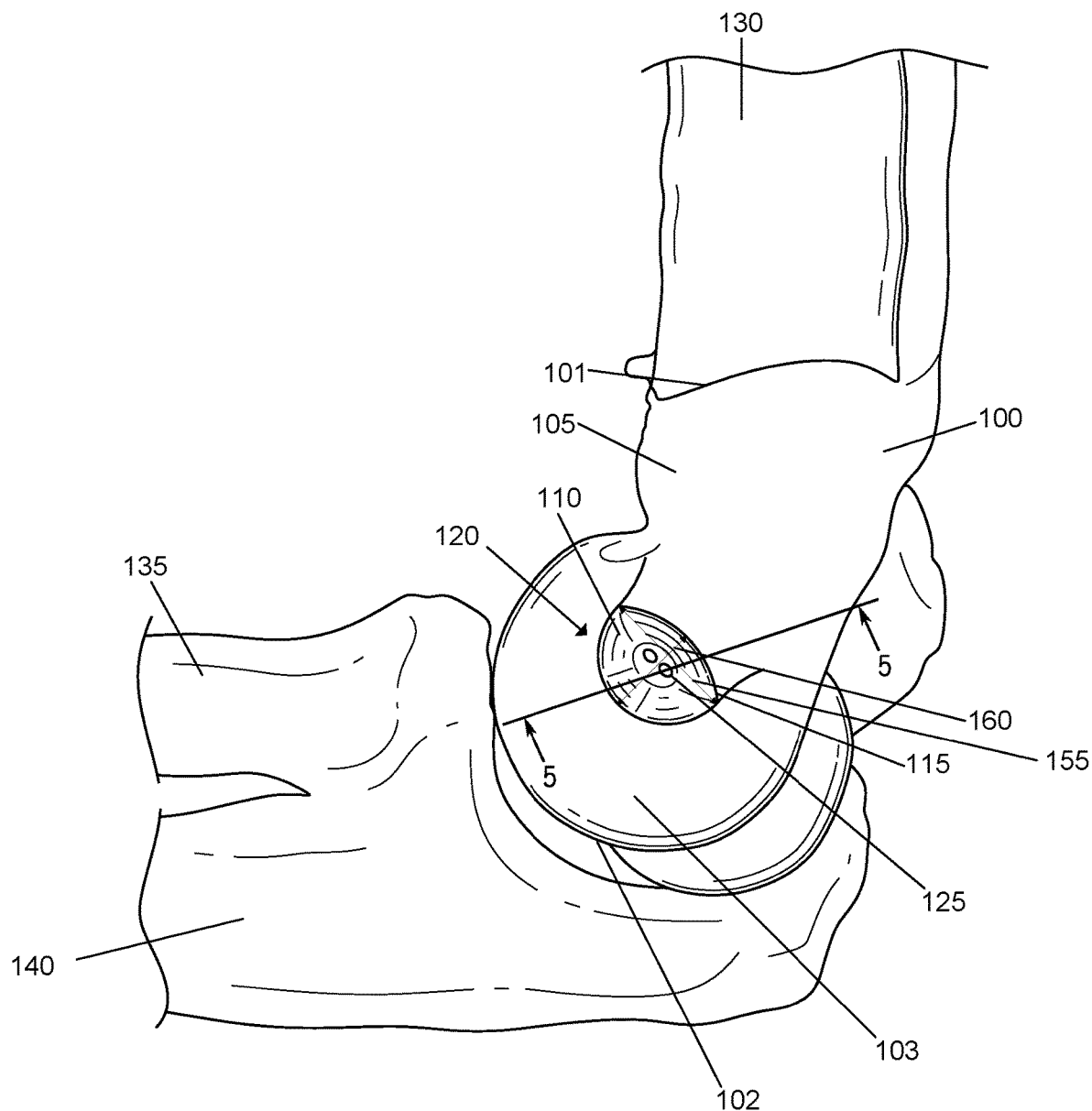
FIG. 1 is a side view of an exemplary elbow implant, according to one embodiment.

According to particular embodiments, this disclosure relates to surgical implants with features for securing a ligament (or other structures) to the implant. As will be understood from discussions herein, it may be advantageous to attach ligaments or other anatomical structures to surgical implants (patient-specific or otherwise) when reconstructing or partially reconstructing certain joints and other areas of the body. For example, when performing an ankle or elbow arthroplasty, the optimal location for reattaching a ligament, tendon, or other structure may be on the implant (e.g., because of the extent of bone replacement with the implant) and it may be challenging to attach a ligament, tendon, or other structure to any remaining portions of bone, but important for joint function.

In at least one embodiment, the implants discussed herein include a docking recess and tunnels that extend at least partially through the device for securing a ligament (or other structure, such as tendon, bone, autograft, or allograft). In some embodiments, the docking recess is formed by the implant and extends a particular depth into the implant. In a particular embodiment, the docking recess connects with two tunnels extending from a cul-de-sac end of the docking recess through to the outer surface of the implant.

In these embodiments (and others), a surgeon may perform the following steps: i) attaching a suture to a ligament, using for example, a Krakow stitch, with the two ends of the suture extending away from the ligament; ii) threading the two ends of the suture through the two tunnels; iii) pulling the ligament into the docking recess via the suture extending through the two tunnels; and iv) tying (or otherwise securing) the sutures over the implant surface between the two tunnels. In this way, in this embodiment, the surgeon secures the ligament to the implant and may allow the ligament to grow into or otherwise adhere to the interior of the docking recess with an improved amount of surface area and an easy-to-use method of tying sutures over the implant bridge between the tunnels.

Furthermore, in some embodiments, a surgeon may salvage and harvest a portion of bone in continuity with an attached ligament. In these embodiments, the bone fragment or plug may be used with a docking recess to improve integration with the implant and help secure the ligament to the docking recess. As will be understood, the bone plug may help facilitate tissue in-growth when the bone plug/ligament is installed within the dock of the implant.

The surgical implant includes, but is not limited to, titanium, cobalt chromium, any suitable ceramic, or any other suitable material. In at least one embodiment, the surgical implant includes a smooth region and/or a textured structure region. According to particular embodiments, the surgical implant includes a plurality of materials, each material associated with a different region or level of roughness or porosity. As discussed herein, in various embodiments, sutures are tied around the implant surface between tunnels. In such areas (e.g., where tied sutures contact a surface of the implant), the implant surface may include a smooth region with a low coefficient of friction to prevent suture degradation (e.g., from the sutures rubbing against the implant surface due to patient movement, internal body forces, etc.).

In some embodiments, the surgical implant includes textured regions that may promote osteo- or other anatomical growth. The textured region may facilitate ingrowth or ongrowth of bone, soft tissue (e.g. allograft, autograft, etc.), or scar tissue to create mechanically sound functional bonds between the tissue structure and the implant. The depth of the textured region or porous ingrowth layer may be between 100 and 500 micrometers wherever surface contact may be expected between implant and bone. For soft tissues, the textured region may differ but typically may be roughened or porous.

The above features (and others) will be discussed herein in the context of specific implant types (e.g., an ankle implant). However, it will be understood that the concepts discussed here are applicable to any suitable implant used anywhere in a human (or other animal).

Referring now to the drawing figures, FIG. 1 shows an exemplary surgical implant 100 within the context of human arm anatomy, according to one embodiment. As shown in FIG. 1, a human arm includes three bones that join together to form the elbow hinge joint. Humerus 130 connects from the shoulder to the elbow forming the top of the hinge joint, and radius 135 and ulna 140 connect the wrist to the elbow forming the bottom portion of the hinge joint. The elbow joint includes three separate joints to perform the "hinge" function—ulnohumeral joint is where movement between the ulna 140 and humerus 130 occurs; radio humeral joint is where movement between the radius 135 and humerus 130 occurs; and proximal radioulnar joint is where movement between the radius 135 and ulna 140 occurs.

In the embodiment shown in FIG. 1, the surgical implant 100 is an elbow implant 100 for replacing a portion of a patient's elbow joint that includes the ulnohumeral, radiohumeral, and proximal radioulnar joints and portions of the humerus 130, radius 135, and ulna 140. The implant 100 is inserted between a patient's humerus 130 on a top face 101 and radius 135 and ulna 140 on a bottom face 102.

In the embodiment shown in FIG. 1, the surgical implant 100 includes a docking recess 120 on a front face 103. In at least one embodiment, the docking recess 120 may be situated on any surface of the surgical implant 100. In some embodiments, the surgical implant 100 may include a plurality of docking recesses 120.

In at least one embodiment, the surgical implant 100 includes a transition area 115. In a particular embodiment, the transition area 115 defines a perimeter of the docking recess 120, which may be a depression or fossa or any other suitable structure. In alternate embodiments, the transition area 115 includes a circular or ovular perimeter of the docking recess 120, but may define any suitable shape of the docking recess 120. As will be discussed with reference to FIG. 5, a depth of the docking recess 120 and other features may be at least partially defined by the transition area 115 and/or docking recess 120 perimeter.

The surface of the surgical implant may have various structures including, but not limited to, smooth and/or textured structures. As will be understood from discussions herein, a textured surface may include any type of rough surface, including, but not limited to, a porous surface, a gyroid surface, a scored, or other roughened surface.

In various embodiments, the smooth region 105 of the implant 100 surface lessens suture degradation and/or performs other functions, including, but not limited to, promoting or facilitating articulation. In one embodiment, the porous and/or the textured portions of the implant 100 surface promote tissue structure ingrowth. As shown in FIG. 1, the docking recess 120 may include any suitable interior surface, surface structure, or surface configuration, and may be formed by any one of or more than one of the aforementioned surface structures. In at least one embodiment, the docking recess 120 is formed by a porous osteointegration region 110 that enables ligament reattachment and promotes ingrowth. In certain embodiments, the implant 100 may include porous osteointegration regions 110 on other/additional surfaces, which may be interspersed with the smooth region 105 wherever bone ingrowth might be advantageous. Furthermore, the porous region 110 is not necessarily also the textured region.

Figure 2:
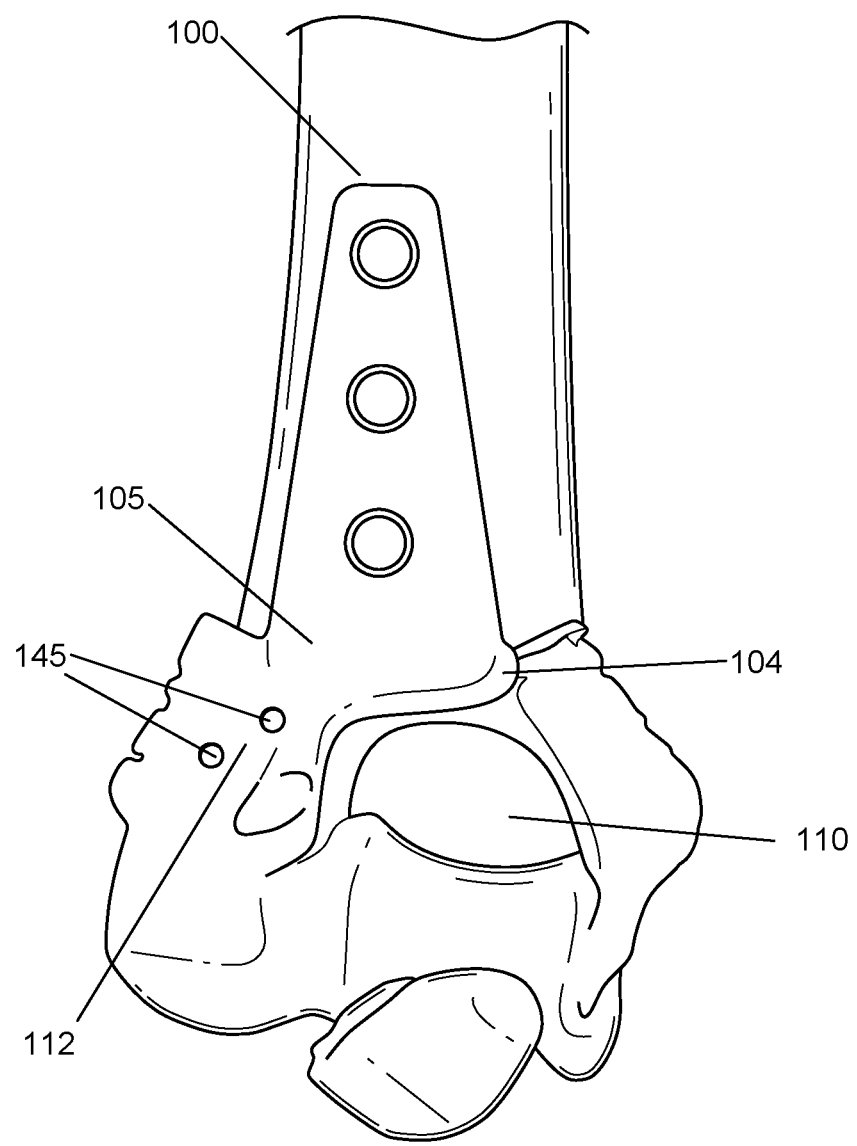
FIG. 2 is a back view of the exemplary elbow implant of FIG. 1, according to one embodiment.

In some embodiments, the docking recess 120 contains a plurality of openings 125 which may be in any suitable shape and size in accordance with the principles of this disclosure. FIG. 2 shows a back surface 104 of the surgical implant 100, according to one embodiment, which includes a plurality of openings 145 on the back surface 104 connected to the plurality of openings 125 within the docking recess 120 (pictured in FIG. 1) to form tunnels 165 (one tunnel shown in FIG. 5). In various embodiments, the openings 145 on the back surface 104 correspond 1:1 with openings 125 within the docking recess 120, and may be in any suitable shape and size in accordance with the principles of this disclosure. In various embodiments, the tunnels 165 between the docking recess openings 125 and the back surface openings 145 allow a clinician to thread sutures through the tunnels 165 of the implant 100 and tie (or otherwise secure the sutures) to hold a ligament or other structure in place within the docking recess 120. Furthermore, in at least one embodiment, the implant includes a smooth region 105 in the area 112 between the openings 145 on the back surface 104 such that sutures tied against this surface do not deteriorate.

Figure 3:
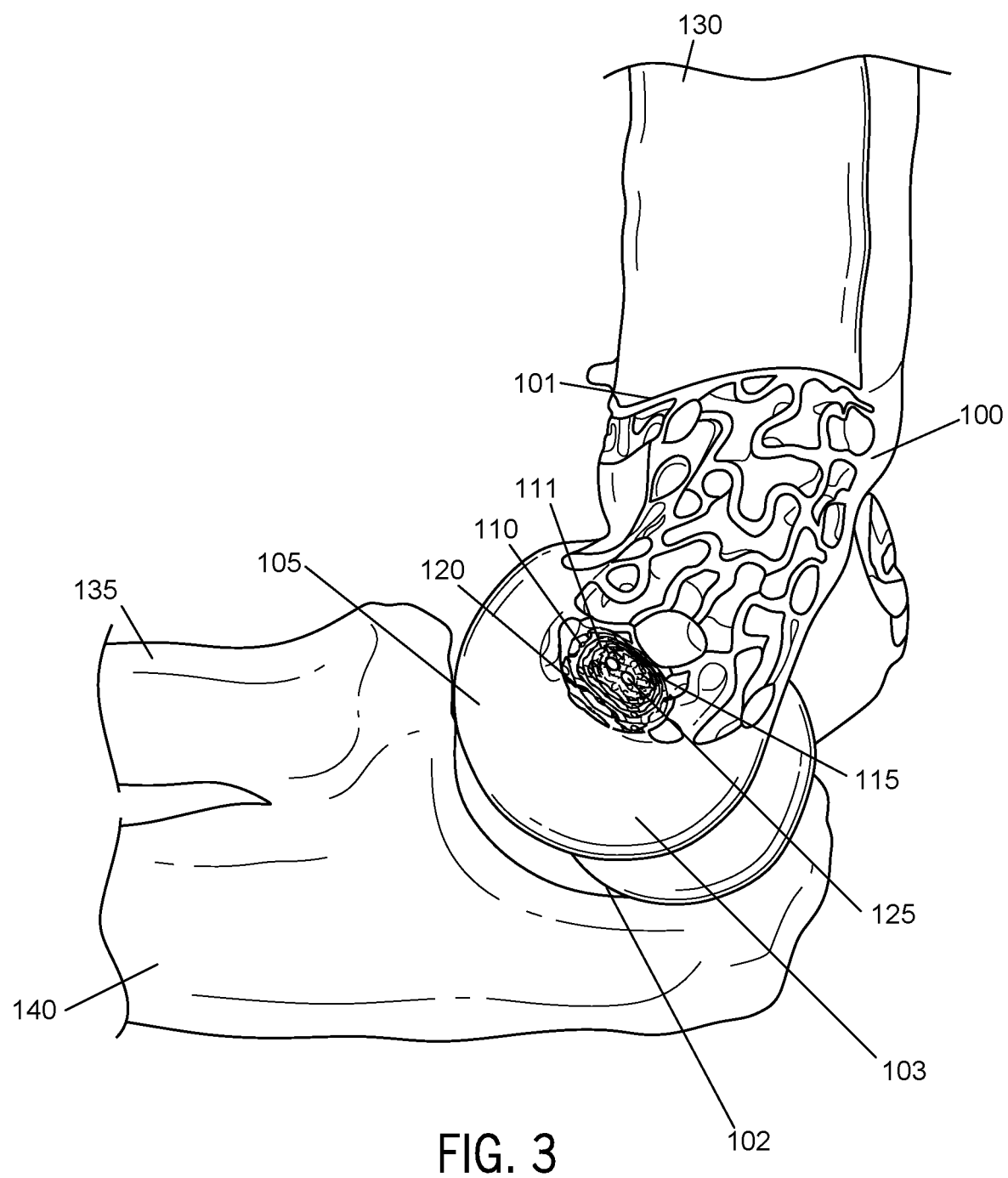
FIG. 3 is a side view of an exemplary elbow implant, according to one embodiment.
Figure 4:
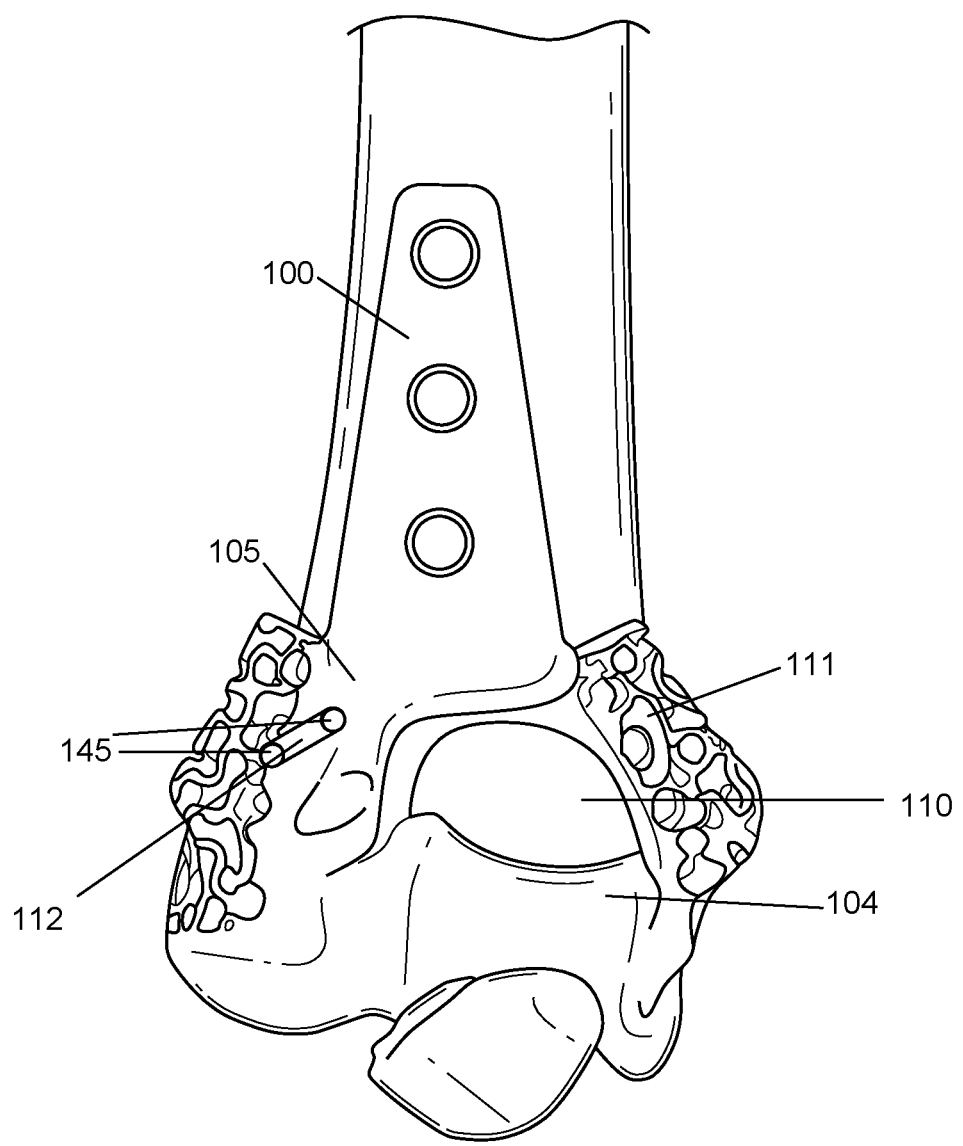
FIG. 4 is a back view of the exemplary elbow implant of FIG. 3, according to one embodiment.

FIGS. 3 and 4 show the surgical implant 100 with optional porous 110 or textured 111 surfaces. Porous or textured surfaces may promote osteo- or other anatomical ingrowth. For example, a porous or textured structure on an exterior of the surgical implant 100 may promote bone ingrowth into the same. As an additional example, a textured structure 111 within the docking recess 120 may promote bone or ligament ingrowth into the same (or at least increased friction to help hold/secure the ligament or bone within the docking recess 120).

Referring now to the embodiment shown in FIG. 3, one example of the interior surface of the docking recess 120 is denoted as a textured structure 111 which may optionally be a gyroid structure according to alternative embodiments. The gyroid structure may be a triply periodic minimal surface (TPMS), or any other suitable design in accordance with the principles of this disclosure. In at least one embodiment, a gyroid structure is beneficial for ligament ingrowth because its porous microstructure facilitates ingrowth therein. The gyroid structure (and/or the entire implant) may be 3D printed in order to obtain a high degree of customizability in the surgical implant 100 for different patient applications.

FIG. 4 shows the surgical implant 100 rotated to show back surface 104 including smooth region 105, porous region 110, and textured region 111. Openings 145 on the back surface 104 connect to form tunnels 165 (pictured in FIG. 5) with openings 125 within the docking recess 120 as shown in FIG. 3. In the embodiment shown, the openings 145 on the back surface 104 correspond with the openings 125 within the docking recess 120, and may be in any suitable shapes and sizes in accordance with the principles of this disclosure. In various embodiments, the area 112 between the openings 145 on the back surface 104 is smooth so that sutures tied against this surface do not deteriorate due to friction against this surface, thereby promoting patient healing.

Figure 5:
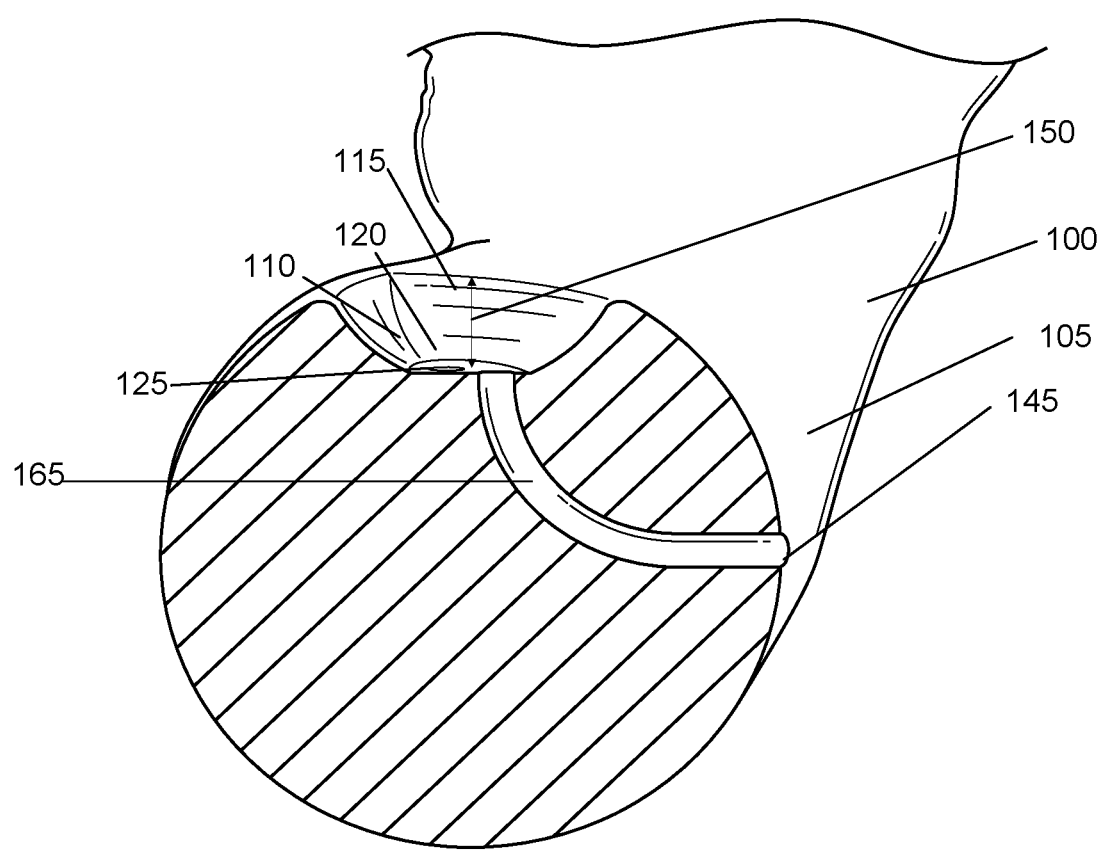
FIG. 5 is a cross section view of the exemplary elbow implant of FIG. 1, according to one embodiment.

FIG. 5 shows a cross-section view of the surgical implant 100 and exemplary dimensions of the docking recess 120. In various embodiments, the docking recess 120 includes a depth 150. In at least one embodiment, the depth 150 is 2 millimeters to 30 millimeters, but this may be any suitable depth.

Referring back to FIG. 1, the transition area 115 may include a major axis 155 and a minor axis 160 approximately defining the perimeter of the docking recess 120. The major axis 155 and the minor axis 160 may be any suitable dimensions. In at least one embodiment, the major axis 155 may be 5 millimeters to 10 millimeters. According to a particular embodiment, the minor axis 160 may be 5 millimeters to 10 millimeters.

Turning back to FIG. 5, in at least one embodiment, the openings 125 within the docking recess 120 connect to the openings 145 on the back surface 104 to form smooth surfaced tunnels 165, thereby allowing a clinician to thread sutures through and tie a tissue structure in place within the docking recess 120. The sutures are tied around the area (not pictured in FIG. 5) between the openings 145 on the back surface 104, so it may be advantageous for the area to be include a portion of the smooth region 105 to keep the sutures intact. Alternative embodiments may have different configurations of back surface openings 145, tunnels 165, and docking recess openings 125, and different resulting paths for sutures in accordance with the principles of this disclosure.

Figure 6:
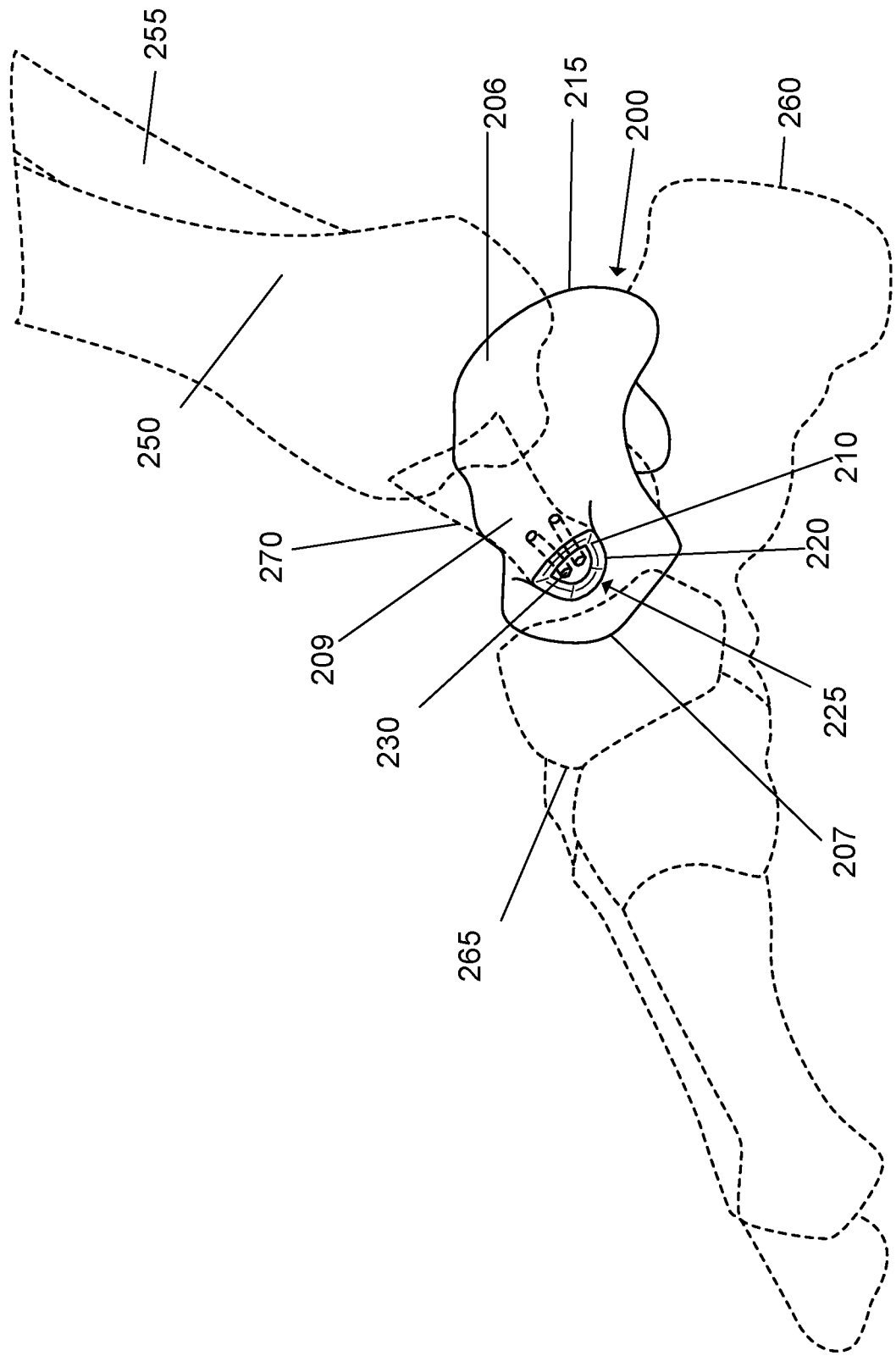
FIG. 6 is a side view of an exemplary talus implant, according to one embodiment.

Now referring to FIG. 6, a surgical implant 200 is shown as an exemplary ankle implant 200 bearing several similarities to the features of the exemplary elbow embodiments of FIGS. 1-5. The human ankle joint is the area where the foot and the leg meet, and it is comprised of three bones that join together to form a hinge joint. Tibia 250 and fibula 255 connect from the knee to the ankle, acting as a mortise and forming the top of the hinge joint in which the body of the talus fits (the lower part of the ankle), and which acts as a tenon. The ankle includes three smaller joints: the talocrural joint, the subtalar joint, and the inferior tibiofibular joint. The movements produced at the overall ankle joint are dorsiflexion and plantarflexion of the foot.

In various embodiments, the surgical implant 200 replaces at least a portion of a patient's talus bone. In at least one embodiment, the surgical implant 200 forms the talocrural, subtalar, and inferior tibiofibular joints with the patient's fibula 255 and tibia 250 and may enable the patient to perform dorsiflexion and plantarflexion foot movements (or may fuse the joints). The surgical implant is inserted between tibia 250 and fibula 255 on a top face 206 and between calcaneus 260 and navicular 265 on a bottom face 207.

In the embodiment shown, the surgical implant 200 includes a docking recess 225 on a back face 209. In embodiments, the docking recess 225 can be situated on any surface of the implant 200, and the implant 200 may contain any suitable number of docking recesses 225. According to at least one embodiment, the surgical implant 200 includes a transition area 220 that defines a perimeter of the docking recess 225, which may be a depression or fossa or any other suitable structure. In alternate embodiments, the transition area 220 includes a circular or ovular perimeter of the docking recess 225, but may define any suitable shape. As will be discussed with reference to FIG. 9, a depth of the docking recess 225 and other features may be at least partially defined by the transition area 220 and/or the docking recess 225 perimeter.

Similar to the exemplary elbow embodiments discussed previously and for similar purposes, the surface of the surgical implant 200 may have various structures including, but not limited to, smooth 215, porous 210, and textured structures. The docking recess 225 may include any suitable interior surface, surface structure, or surface configuration, and may be formed by any one of or more than one of the aforementioned surface structures.

Figure 7:
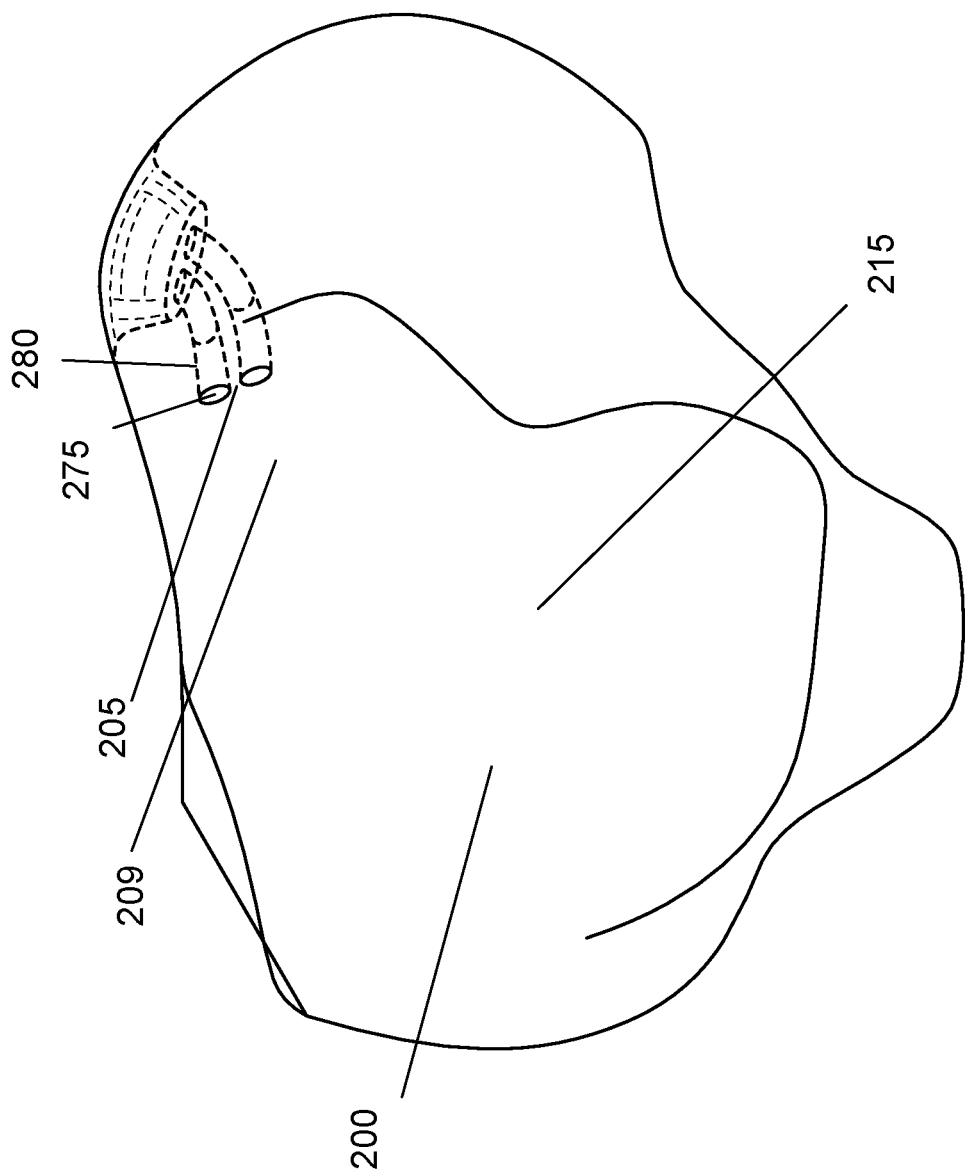
FIG. 7 is a top view of the exemplary talus implant of FIG. 6, according to one embodiment.

In some embodiments, the docking recess 225 defines a plurality of openings 230 which may be in any suitable shape and size in accordance with the principles of this disclosure. FIG. 7 shows a back surface 209 of the surgical implant 200, according to one embodiment, which includes a plurality of openings 275 on the back surface 209 connected to the plurality of openings 230 within the docking recess 225 to form tunnels 280. In various embodiments, the openings 275 on the back surface 209 correspond 1:1 with openings 230 within the docking recess 225, and may be in any suitable shape and size in accordance with the principles of this disclosure. The tunnels 280 between the docking recess openings 230 and the back surface openings 275 allow a clinician to thread sutures through the tunnels 280 of the implant 200 and tie (or otherwise secure the sutures) to hold a ligament or other structure in place within the docking recess 225. Furthermore, in at least one embodiment, the implant 200 includes a smooth region 215 in an area 205 between the openings 275 on the back surface 209 such that sutures tied against the area 205 do not deteriorate.

In the embodiment shown in FIG. 6, a tissue structure 270 such as an anterior tibiotalar ligament may project from an attachment point on the tibia 250 and be attached to the docking recess 225 where a clinician may use sutures to tie the tissue structure 270 in place via openings 230 within the docking recess 225, but alternative embodiments may utilize any tissue structure 270 and any placement of a docking recess 225 on the implant 200.

Figure 8:
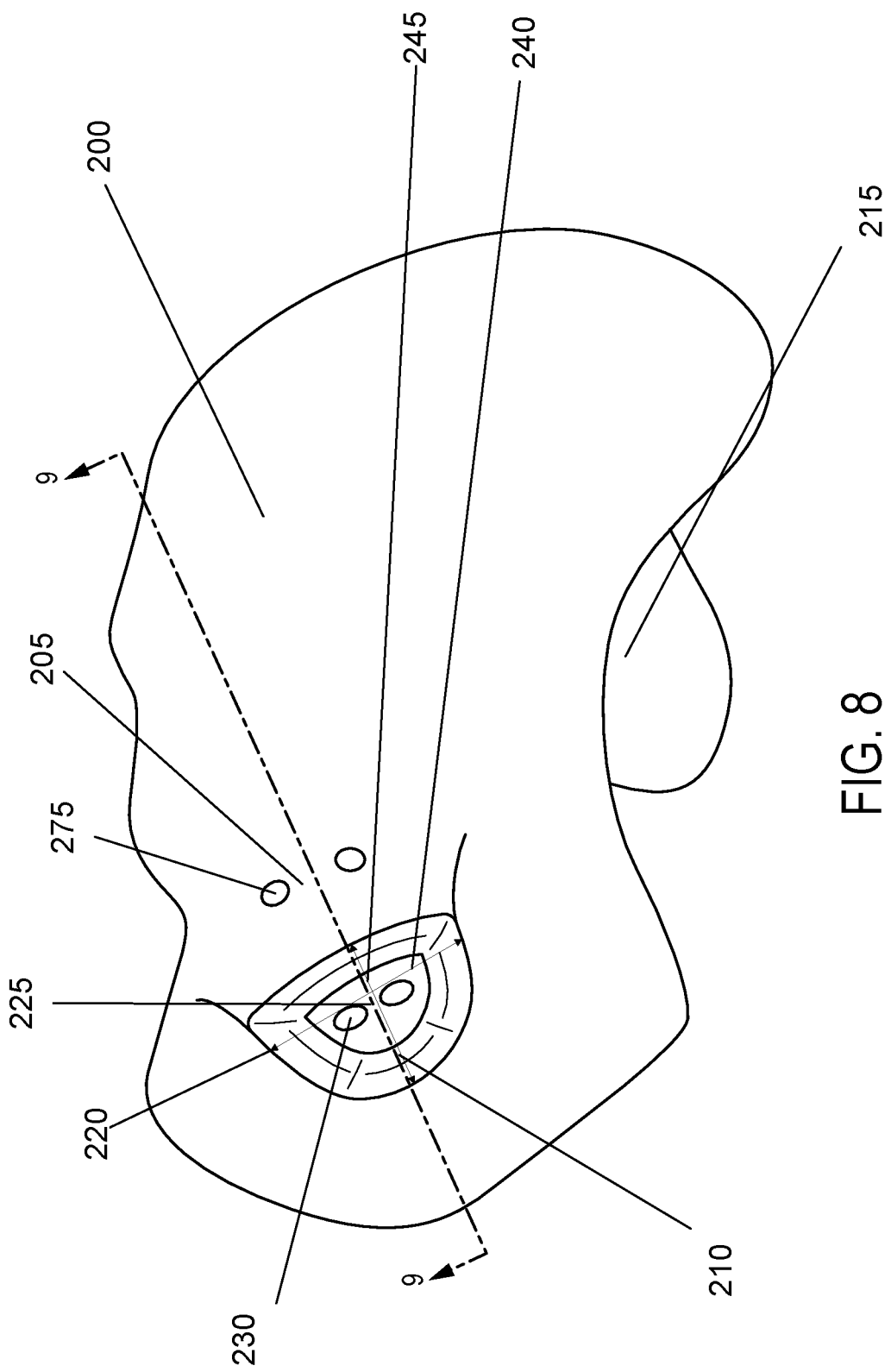
FIG. 8 is a side view of the exemplary talus implant of FIG. 6, according to one embodiment.
Figure 9:
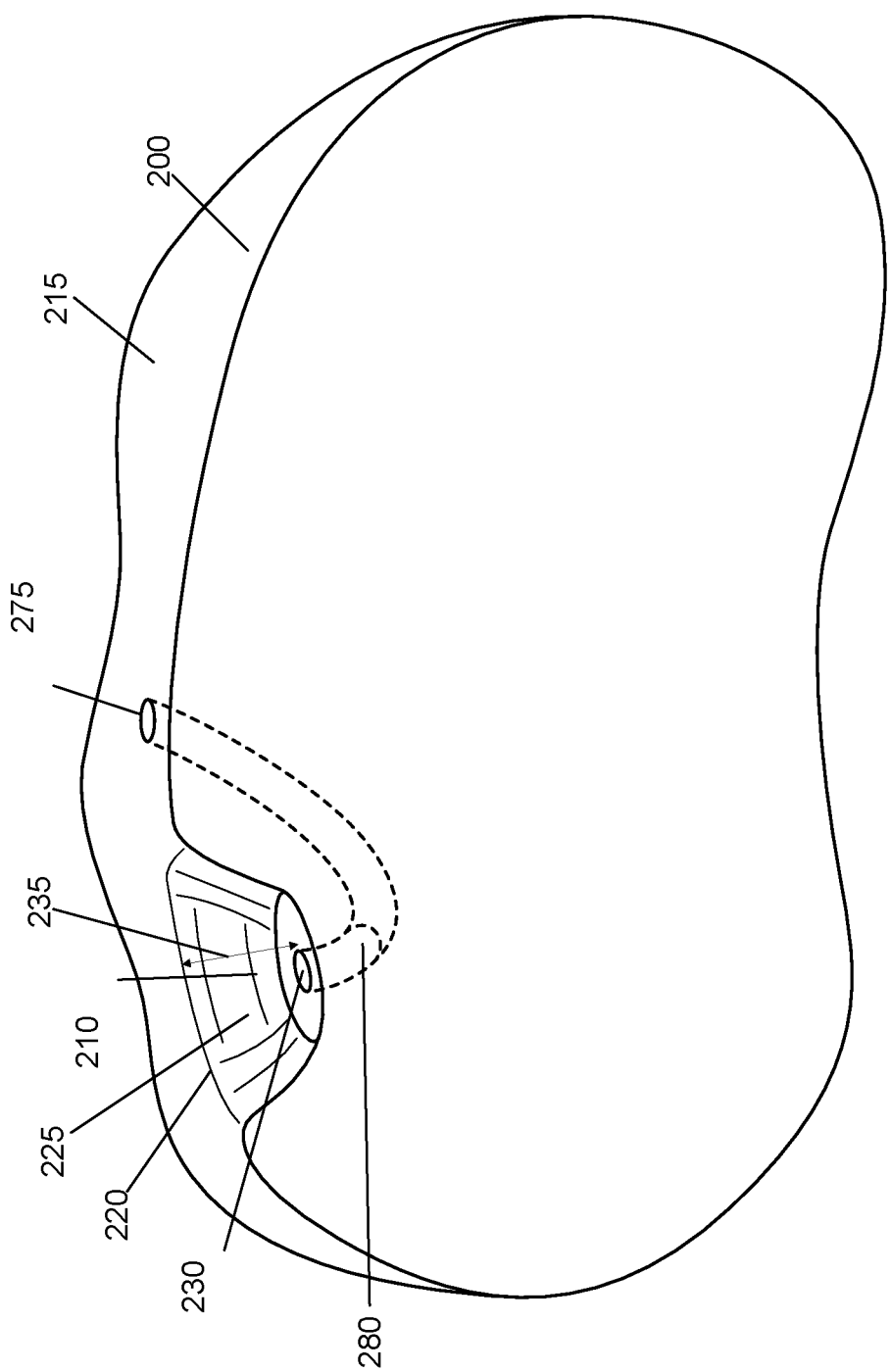
FIG. 9 is a section view of the exemplary talus implant of FIG. 8, according to one embodiment.

FIG. 8 shows a view of the surgical implant 200 transected by a cut line resulting in the view of FIG. 9. The transition area 220 may include a major axis 240 and a minor axis 245 approximately defining the perimeter of the docking recess 225. The major axis 240 and the minor axis 245 may be any suitable dimensions. In at least one embodiment, the major axis 240 may be 5 millimeters to 10 millimeters. According to a particular embodiment, the minor axis 245 may be 5 millimeters to 10 millimeters.

FIG. 9 shows a cross-section view of the surgical implant 200 and exemplary dimensions of the docking recess 225. In various embodiments, the docking recess 225 includes a depth 235. In at least one embodiment, the depth 235 is 2 millimeters to 30 millimeters, but this may be any suitable depth.

Figure 10:
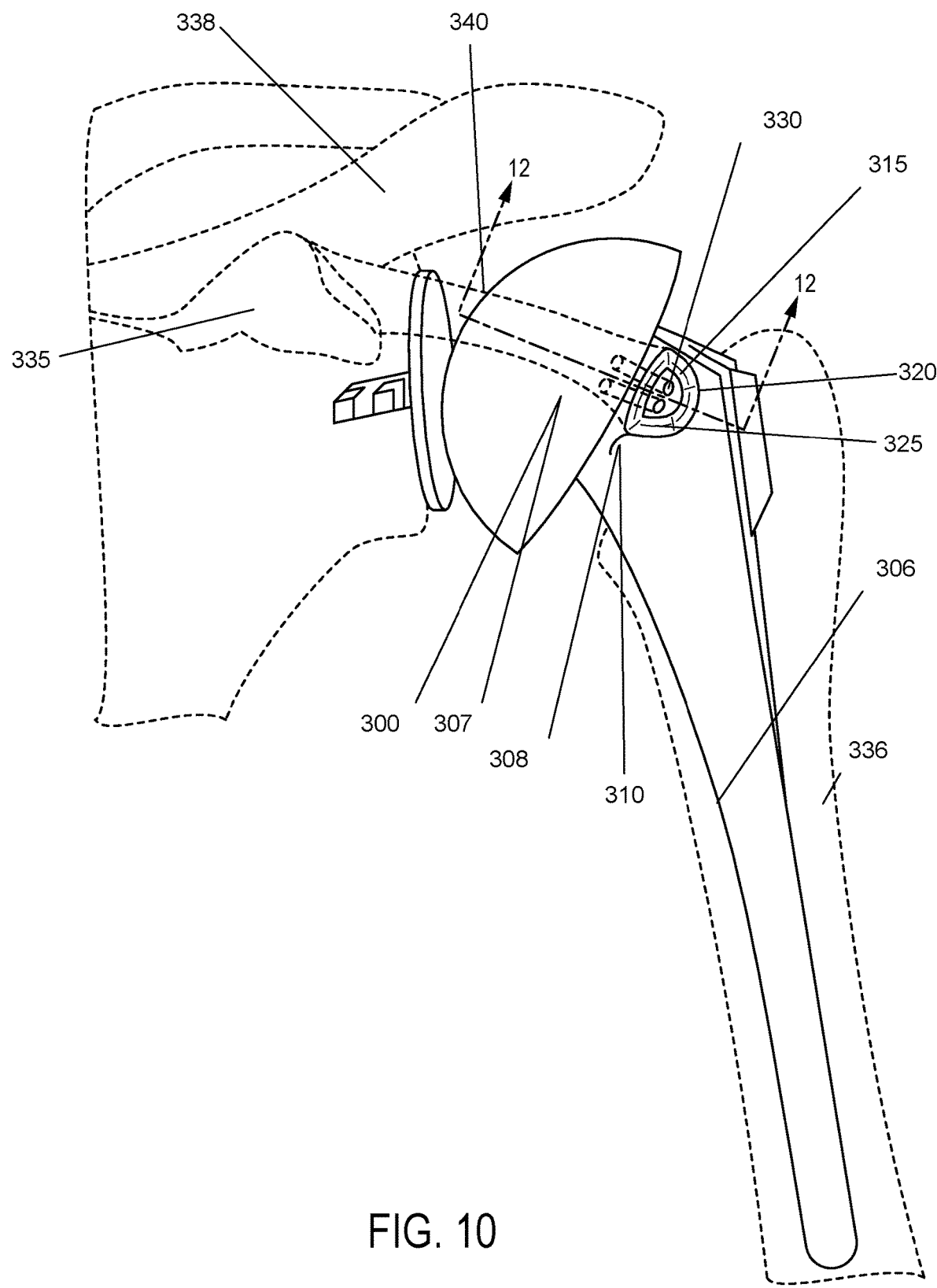
FIG. 10 is a side view of an exemplary shoulder implant, according to one embodiment.

Referring now to FIG. 10, the surgical implant 300 shown is an exemplary shoulder implant 300 bearing several similarities to the features of the exemplary elbow and ankle embodiments of FIGS. 1-9. The human shoulder is formed by a clavicle 338, scapula 335, and humerus 336, and the shoulder joint comprises the part of the body where the humerus 336 attaches to the scapula 335 (the humeral head sits in the glenoid cavity). Generally speaking, the shoulder is a ball and socket joint that allows the arm to rotate in a circular fashion or to hinge out and up away from the body.

In the embodiment shown, the surgical implant 300 replaces a portion of the patient's humerus 336 including a ball and cap 307 and a part of the humeral stem 306. In various embodiments, the surgical implant 300 is inserted between the scapula 335 and a portion of the humerus 336 to form the major shoulder joint. As will be understood from discussions herein, the surgical implant 300 shown is a traditional total shoulder implant, but the implants contemplated herein may be any suitable implant, including partial or reverse shoulder implants (among any other type of implant that might benefit from tissue attachment).

The surgical implant 300 includes a docking recess 325 on a front face 308. In other embodiments, the docking recess 325 can be situated on any surface of the implant 300 and the implant 300 may contain any suitable number of docking recesses 325. The surgical implant 300 includes a transition area 320 that defines a perimeter of the docking recess 325, which may be a depression or fossa or any other suitable structure. In alternate embodiments, the transition area 320 includes a circular or ovular perimeter of the docking recess 325, but may define any suitable shape. As will be discussed with reference to FIG. 12, a depth of the docking recess 325 and other features may be at least partially defined by the transition area 320 and/or docking recess 325 perimeter.

Similar to the exemplary elbow embodiments discussed previously and for similar purposes, the surface of the surgical implant 300 may have various structures including, but not limited to, smooth 310, porous 315, and textured structures. The docking recess 325 may include any suitable interior surface, surface structure, or surface configuration, and may be formed by any one of or more than one of the aforementioned surface structures.

Figure 11:
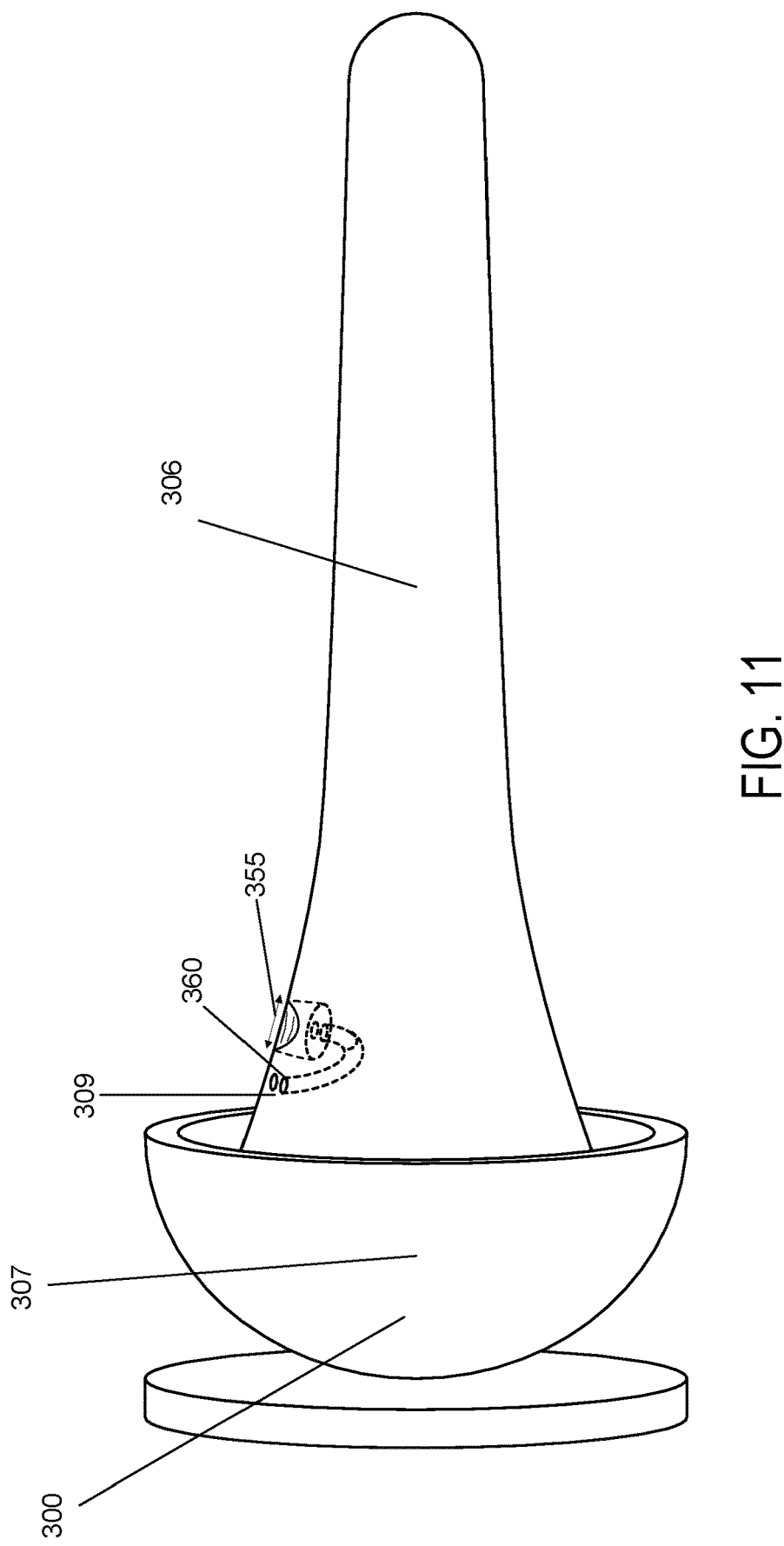
FIG. 11 is a side view of the exemplary shoulder implant of FIG. 10, according to one embodiment.

The docking recess 325 contains a plurality of openings 330 which may be in any suitable shapes and sizes in accordance with the principles of this disclosure. FIG. 11 shows a side view of the surgical implant 300, which includes a plurality of openings 360 on the front face 308 connected to the plurality of openings 330 within the docking recess 325 shown in FIG. 10 to form smooth surfaced tunnels 365 (pictured in FIG. 12). This allows a clinician to thread sutures through the tunnels 365 of the implant 300 to secure a tissue structure in place within the docking recess 325. In addition to the tunnels 365, an area 309 between the openings 360 on the front face 308 is smooth so that sutures secured against this surface do not deteriorate due to friction against this surface In various embodiments, the docking recess 325 contains a plurality of openings 330. In the embodiment shown in FIG. 10, a tissue structure 340 such as a coracohumeral ligament 340 may project from an attachment point on the coracoid process of the scapula 335 and be attached to the docking recess 325 where sutures may tie the ligament in place via openings 330 within the docking recess 325, but alternative embodiments may utilize any tissue structure 340 and any placement of a docking recess 325 on implant 300.

Figure 12:
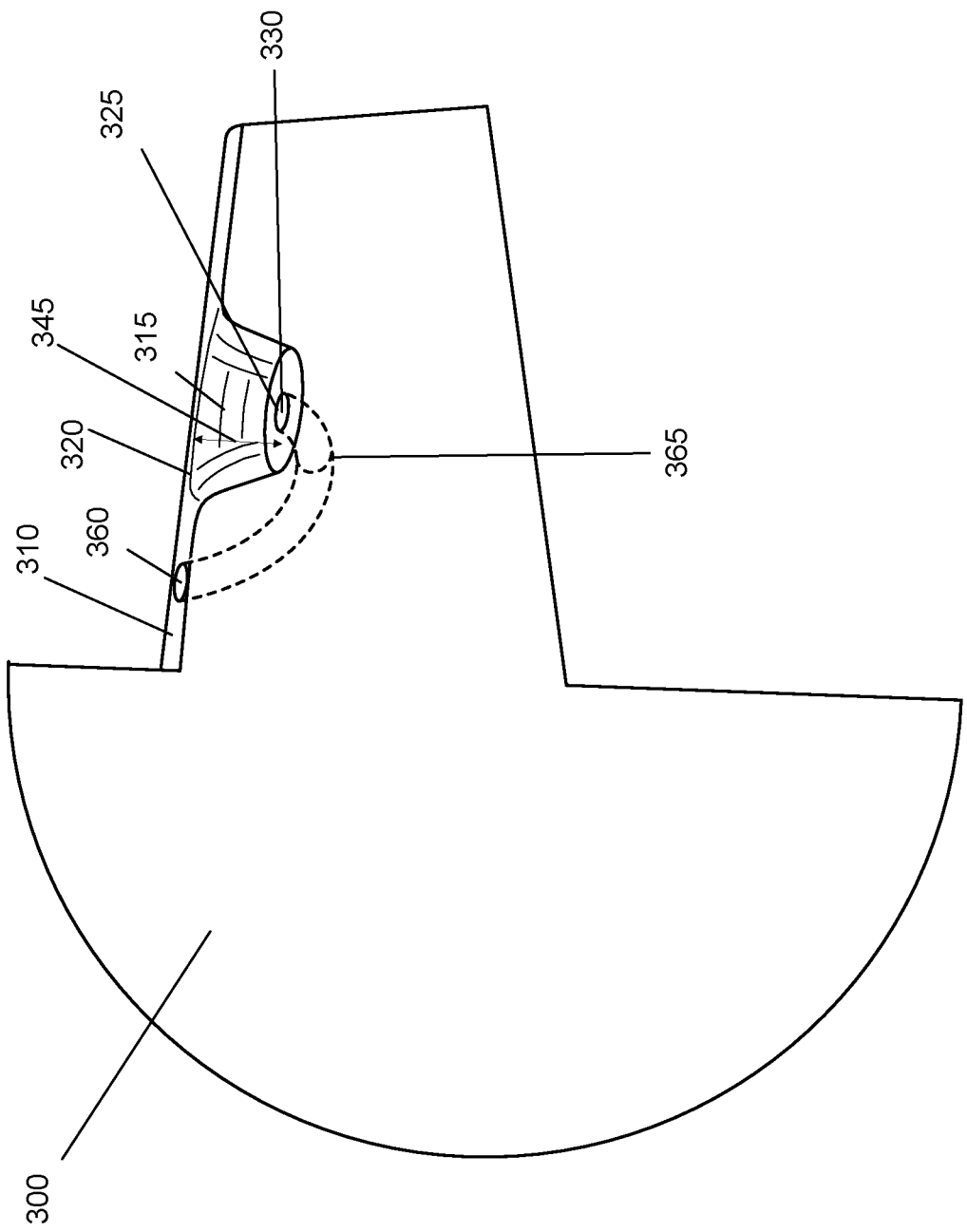
FIG. 12 is a section view of the exemplary shoulder implant of FIG. 10, according to one embodiment.

The surgical implant 300 of FIG. 10 is transected by a cut line resulting in the view of FIG. 12. The transition area 320 may include a major axis (which is similar to aforementioned embodiments) and a minor axis 355 approximately defining the perimeter of the docking recess 325. The major axis and the minor axis 355 may be any suitable dimensions. In at least one embodiment, the major axis may be 5 millimeters to 10 millimeters. According to a particular embodiment, a minor axis 355 may be 5 millimeters to 10 millimeters.

FIG. 12 shows a cross-section view of the surgical implant 300 and exemplary dimensions of the docking recess 325. In various embodiments, the docking recess 325 includes a depth 345. In at least one embodiment, the depth 345 is 2 millimeters to 30 millimeters, but this may be any suitable depth.

Figure 13:
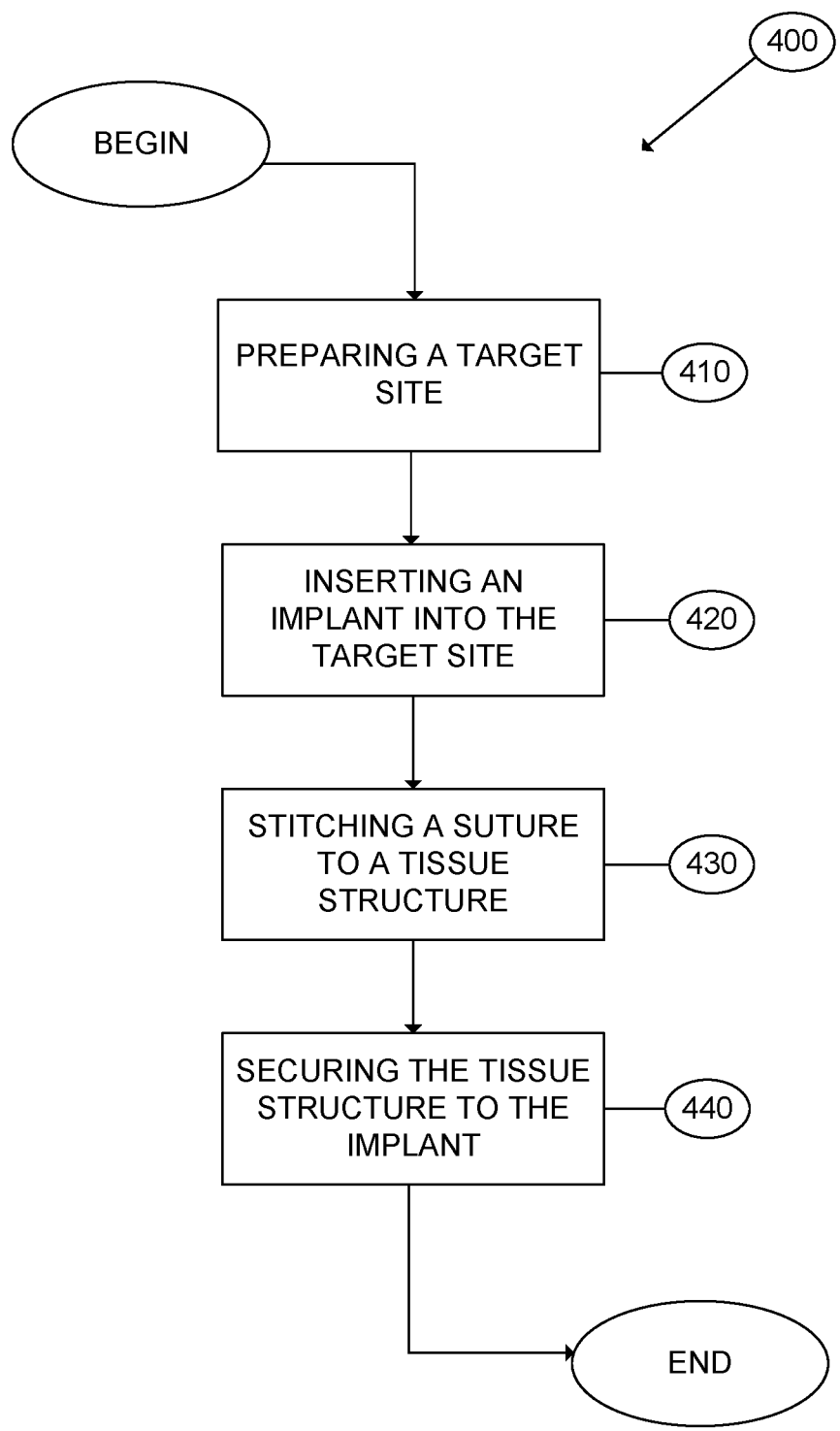
FIG. 13 is a flow chart of an exemplary surgical process, according to one embodiment.

Turning now to FIG. 13, the figure describes a method 400 for securing a tissue to an implant. In the context of a talus-replacing ankle surgery, the method includes: 1) preparing a target site of the patient 410; 2) inserting an implant into the target site 420; 3) stitching one or more sutures to one or more tissue structures 430; 4) securing the tissue structures to the implant 440 via any suitable attachment mechanism including, but not limited to, Krackow stitching. The clinician threads sutures through the tunnels and out through the openings within docking recess, and ties the sutures to secure the tissue within the implant.

Figure 14:
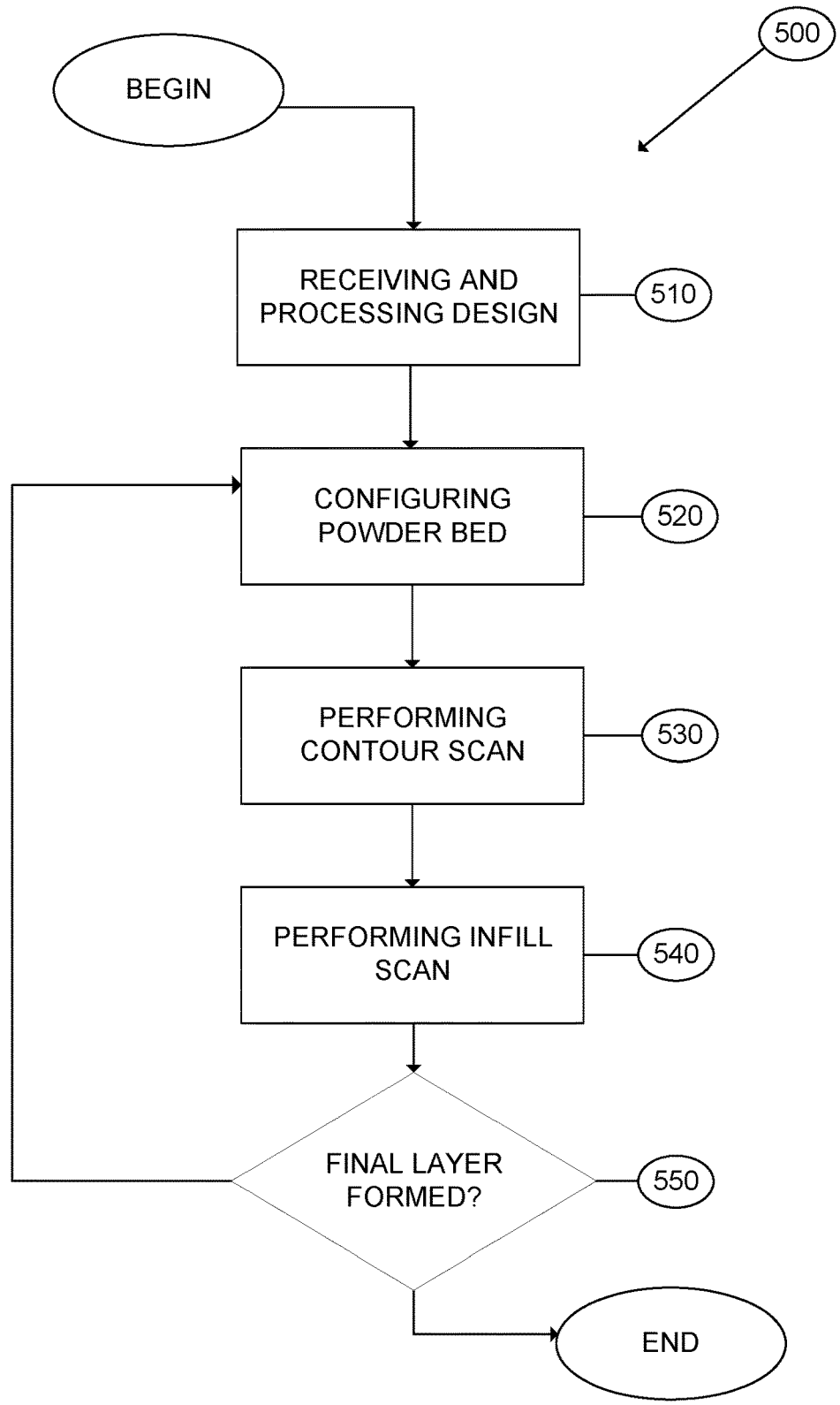
FIG. 14 is a flow chart of an exemplary implant manufacturing process, according to one embodiment.

Referring now to FIG. 14, in at least one embodiment, the surgical implant structures are produced by additive manufacturing methods, such as, for example, laser powder bed fusion, including, but not limited to, selective laser melting (SLM) processes. As described herein, a laser powder bed fusion process refers to a technique of iteratively lasing and melting a (typically metal) powder material into stacked patterns to create a layered, three-dimensional structure. The process 500 generally includes: 1) receiving and processing a design 510; 2) configuring powder bed 520; 3) performing contour scan 530; 4) performing infill scan 540; and 5) determining whether the final layer of the design is formed 550. If the final layer of the design is formed, in the embodiment shown in FIG. 14, the process ends. According to one embodiment, if the final layer of the design is not formed (e.g., there are more layers to form), then the process returns to the second step 520. Exemplary processes for producing one of more implants described herein can be found in the following patent and patent application incorporated herein by reference as if set forth in their entireties:

U.S. Pat. No. 11,026,798, issued on Jun. 8, 2021, and entitled SHEET BASED TRIPLY PERIODIC MINIMAL SURFACE IMPLANTS FOR PROMOTING OSSEOINTEGRATION AND METHODS FOR PRODUCING SAME; and U.S. patent application Ser. No. 17/314,378, filed on May 7, 2021, and entitled SPATIALLY VARIED IMPLANTS AND PROCESSES FOR MAKING AND USING SAME.

ALTERNATE EMBODIMENTS

It is understood that the present disclosure is highly customizable, and any type of implant can be configured with any number and placement of docking recesses of any shape and size to receive any number and type of tissue attachment. Various alternate embodiments are contemplated herein.

As will be understood, patient ligaments may be of different sizes, only portions of ligaments may be salvageable, and/or bone plugs may be of different sizes (e.g., if a ligament is harvested with a portion of bone to be placed within a docking recess). In at least some embodiments, the result might be an inconsistency between pre-operative imaging and operative ligament sizes for attaching within a docking recess. In an alternate embodiment to solve this potential ligament/bone plug size variation, the docking recess (e.g., docking recess 225) is "removeable." In this embodiment, a patient-specific implant (e.g., surgical implant 200) is created based on patent images and/or other suitable pre-operative data. Continuing with this embodiment, the patient-specific implant is customized to the patient, but has a "standard" size docking area. Still continuing with this embodiment, a surgical kit includes the patient-specific implant, along with one or more docking recesses of various sizes that fit within the standard size docking area. In this way, in this embodiment, the surgeon can select one of the one or more docking recesses included in the surgical kit that best suits the salvageable ligament or bone plug. Still continuing with this embodiment, once the surgeon selects a docking recess, the surgeon attaches the ligament (with or without bone plug) to the selected docking recess and/or installs the selected docking recess within the standard sized docking area. As will be understood, the selected docking recess may be locked or attached to an implant in any suitable way, including, but not limited to by a locking/mating mechanism, via hardware (e.g., a screw, nail, etc.), and by press fit (e.g., the selected docking recess is press-fit into a corresponding hole/structure in the implant).

In an alternate embodiment, an allograft may be secured to the docking recess instead of or in addition to the native tissue structure via securing techniques as described above. In this embodiment, a ligament, tendon, bone plug, and/or allograft, amongst other structures, may be pulled into the docking recess and transfixed by means of a screw, bolt, nail, staple, or any other suitable mechanism to hold the tissue structure securely within the docking recess.

In another embodiment, methods to harvest a bone plug of an appropriate size for the docking recess include cylindrical osteotomes, having a notch or notches to slide around the tissue structure, that may core out a bone plug of a defined radius.

The docking recesses discussed herein may include any number and shape of "tunnels." In at least one embodiment, a particular docking recess defines a single hole and tunnel for multiple ends of a suture (or multiple sutures). In this embodiment (and others), the implant with the docking recess includes one or more mechanisms for attaching the multiple ends of the suture, such as, for example, a post, hook, recess with a hook or post, or other mechanism.

According to particular embodiments, the present implants are included in a kit that also includes various instruments, including, but not limited to, instruments for installing a dock (when the dock is "removeable"), hardware for attaching tissue to the dock (e.g., screws, staples, nails, etc.), instruments to aid in threading a suture through a dock or other tunnel or hole, and instruments for installing an implant that includes a dock.

What is claimed is:

1. A method for securing tissue to an implant comprising:
preparing a target site of a subject;
inserting an implant into the target site, the implant comprising:
a docking recess defining a perimeter of about 5 to 10 millimeters, and configured to receive one or more tissue structures and defining at least one opening extending from the docking recess through an outer surface of the implant, wherein the at least one opening is configured to receive a suture and the implant comprises a transition area between the outer surface and the docking recess;
the outer surface comprising:
a porous osteointegration region; and
at least one smooth region, the at least one smooth region comprising a lower coefficient of friction than the porous osteointegration region;
stitching the suture to the one or more tissue structures, wherein the one or more tissue structures comprise a portion of bone attached to a ligament of the subject; and
securing the one or more tissue structures to the implant by:
threading the suture through the implant via the at least one opening;
inserting the one or more tissue structures into the docking recess; and
securing the suture over the at least one smooth region.

2. The method of claim 1, wherein the transition area comprises a perimeter defining a depression or fossa.

3. The method of claim 1, wherein the docking recess comprises a back surface opposite the transition area.

4. The method of claim 3, wherein the back surface defines the at least one opening.

5. The method of claim 4, wherein the docking recess comprises a depth between the transition area to the back surface.

6. The method of claim 5, wherein the depth is 2 millimeters to 30 millimeters.

7. The method of claim 5, wherein the docking recess comprises one or more side surfaces between the transition area and the back surface.

8. The method of claim 7, wherein at least one of the back surface and the one or more side surfaces comprise a porous structure.

9. The method of claim 8, wherein the porous structure comprises a textured structure.

10. The method of claim 8, wherein the porous structure comprises a gyroid structure.

11. A method for securing tissue to an implant comprising:
preparing a target site of a subject;
inserting an implant into the target site, the implant comprising:
an outer surface, the outer surface comprising:
a porous osteointegration region; and
at least one smooth region, the at least one smooth region comprising a lower coefficient of friction than the porous osteointegration region;
a docking recess, the docking recess having a back surface at a depth extending partially into the implant, and configured to receive one or more tissue structures and defining at least one opening extending from the back surface through the implant to the outer surface, wherein the at least one opening is configured to receive a suture; and
a transition area between the outer surface and the docking recess defining a perimeter of about 5 to 10 millimeters;
stitching the suture to the one or more tissue structures; and
securing the one or more tissue structures to the implant by:
threading the suture through the implant via the at least one opening;
inserting the one or more tissue structures into the docking recess; and
securing the suture over the at least one smooth region.

12. The method of claim 11, wherein the one or more tissue structures comprise a ligament of the subject.

13. The method of claim 12, wherein the one or more tissue structures comprise a portion of bone attached to the ligament of the subject.

14. The method of claim 13, wherein the transition area comprises a perimeter defining a depression or fossa.

15. The method of claim 13, wherein the docking recess comprises a back surface opposite the transition area.

16. The method of claim 15, wherein the back surface defines the at least one opening.

17. The method of claim 16, wherein the docking recess comprises a depth between the transition area to the back surface.

18. The method of claim 17, wherein the depth is 2 millimeters to 30 millimeters.

19. The method of claim 17, wherein the docking recess comprises one or more side surfaces between the transition area and the back surface.

20. The method of claim 19, wherein at least one of the back surface and the one or more side surfaces comprise a porous structure.

21. The method of claim 20, wherein the porous structure comprises a textured structure.

22. The method of claim 19, wherein the porous structure comprises a gyroid structure.

* * * * *